United States Patent
Peterson et al.

(10) Patent No.: US 9,636,419 B2
(45) Date of Patent: May 2, 2017

(54) TARGETING MULTIPLE RECEPTORS ON A CELL SURFACE FOR SPECIFIC CELL TARGETING

(71) Applicants: The University of Kansas, Lawrence, KS (US); Albert Einstein College of Medicine, Inc., Bronx, NY (US)

(72) Inventors: Blake R. Peterson, Lawrence, KS (US); Liang Xu, Lawrence, KS (US); Matthew Levy, New Rochelle, NY (US)

(73) Assignees: The Universit of Kansas, Lawrence, KS (US); Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 14/512,862

(22) Filed: Oct. 13, 2014

(65) Prior Publication Data
US 2015/0190529 A1    Jul. 9, 2015

Related U.S. Application Data

(60) Provisional application No. 61/889,816, filed on Oct. 11, 2013.

(51) Int. Cl.
*A61K 38/00* (2006.01)
*A61K 47/48* (2006.01)

(52) U.S. Cl.
CPC .. *A61K 47/48569* (2013.01); *A61K 47/48038* (2013.01); *A61K 47/48746* (2013.01)

(58) Field of Classification Search
CPC ............................ A61K 2300/00; A61K 38/00
See application file for complete search history.

(56) References Cited

U.S. PATENT DOCUMENTS

| | | | |
|---|---|---|---|
| 8,637,468 B2 | 1/2014 | Peterson | |
| 8,889,631 B2* | 11/2014 | Peterson | ........................ 514/1.2 |
| 2010/0041773 A1 | 2/2010 | Peterson | |
| 2015/0174265 A1* | 6/2015 | Wittrup | .............. C07K 16/1282 424/172.1 |

FOREIGN PATENT DOCUMENTS

WO    2014055754 A1    4/2014

\* cited by examiner

*Primary Examiner* — Karen Cochrane Carlson
(74) *Attorney, Agent, or Firm* — Maschoff Brennan

(57) ABSTRACT

A method of delivering a cargo agent into cytosol of a cell can include: providing the delivery system of one of the embodiments described herein having the first and second delivery platforms; and administering the delivery system to a cell so as to cause targeting of two features on the cell so as to: cause endocytosis of the first and second delivery platforms of the delivery system into a common endosome, destabilize the endosome of the cell having the delivery system, release the cargo agent from the second linker; and release the cargo agent from the destabilized endosome into cytosol of the cell. A method of treating a disease can include: performing the method of method of delivering a cargo agent into cytosol of a cell in a subject having a disease, wherein the cargo agent is a therapeutic agent for the disease.

17 Claims, 11 Drawing Sheets

(A) Representative IgG-auristatin conjugate (14)

(B) Representative IgG-endosome disruptor conjugate (15)

DUPA-HDA-AOC-3Glu-Disulfide Fluorescein

DUPA-HDA-AOC-3Glu-Disulfide Fluorescein
+ Endosome disruptive peptide ED217

SEQUENCE LISTING

```
<160> NUMBER OF SEQ ID NOS: 17

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Ala Trp Trp Ser Tyr Trp Pro Pro Val Ala
1               5                   10

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cholesterol carbamate
```

```
<220> FEATURE:
<221> NAME/KEY: MOD_RES
<222> LOCATION: (1)..(2)
<223> OTHER INFORMATION: Beta-Ala
<220> FEATURE:
<221> NAME/KEY: misc_feature
<222> LOCATION: (4)..(5)
<223> OTHER INFORMATION: Residues at these positions are non-consecutive
      and are separated by a mPEG moiety
<220> FEATURE:
<221> NAME/KEY: MOD_RES
<222> LOCATION: (5)..(8)
<223> OTHER INFORMATION: Beta-Ala
<220> FEATURE:
<221> NAME/KEY: MOD_RES
<222> LOCATION: (9)..(12)
<223> OTHER INFORMATION: Aib
<220> FEATURE:
<223> OTHER INFORMATION: C-term CONH2

<400> SEQUENCE: 2

Ala Ala Glu Glu Ala Ala Ala Ala Xaa Xaa Xaa Xaa Trp Trp Ala Trp
1               5                   10                  15

Tyr Pro Pro Val Val
            20

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Aib
<220> FEATURE:
<223> OTHER INFORMATION: C-term CONH2

<400> SEQUENCE: 3

Xaa Xaa Xaa Xaa Trp Trp Ala Trp Tyr Pro Pro Val Val
1               5                   10

<210> SEQ ID NO 4
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggaccgaaa aagaccugac uucuauacua agucuacguu ccc                     43

<210> SEQ ID NO 5
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaggacga ugcggaucag ccauguuuac gucacuccuu gucaauccuc aucggc       56

<210> SEQ ID NO 6
<211> LENGTH: 39
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 6 ggggaggacga ugcggaucag ccauguuuac gucacuccu                             39

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molcule:
      Synthetic oligonucleotide

<400> SEQUENCE: 7
gggggaucaa uccaagggac ccggaaacgc ucccuuacac ccct                       44

<210> SEQ ID NO 8
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggacggauuu aaucgccgua gaaagcaugu caaagccgga accgucc                    47

<210> SEQ ID NO 9
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gccuuaguaa cgugcuuuga ugucgauucg acaggaggc                             39

<210> SEQ ID NO 10
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cacgacgcug auggaucguu acgacuagca ucgc                                  34

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgacugguu acccggucg                                                   19
```

```
<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttggtggtgg tggttgtggt ggtggtgg                                          28

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atctaactgc tgcgccgccg ggaaaatact gtacggttag a                           41

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcagcggtgt gggggcagcg gtgtgggggc agcggtgtgg gg                          42

<210> SEQ ID NO 15
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
agccgcgagg ggagggauag gguagggcgc ggcu                                   34

<210> SEQ ID NO 16
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggguucuacg auaaacgguu aaugaucagc uuauggcugg caguuccc                    48

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cit
```

```
<220> FEATURE:
<221> NAME/KEY: misc_feature
<222> LOCATION: (2)..(3)
<223> OTHER INFORMATION: Residues at these positions are non-consecutive
      and are separated by two consecutive mPEG moieties
<220> FEATURE:
<221> NAME/KEY: MOD_RES
<222> LOCATION: (3)..(6)
<223> OTHER INFORMATION: Aib
<220> FEATURE:
<223> OTHER INFORMATION: C-term NH2

<400> SEQUENCE: 17

Val Xaa Xaa Xaa Xaa Xaa Trp Tyr Ala Trp Tyr Ala Trp Tyr Pro Pro
1               5                   10                  15

Val Val
```

TARGETING MULTIPLE RECEPTORS ON A CELL SURFACE FOR SPECIFIC CELL TARGETING

CROSS-REFERENCE

This patent application claims priority to U.S. Provisional Application No. 61/889,816 filed Oct. 11, 2013, which provisional application is incorporated herein by specific reference in its entirety.

GOVERNMENT SUPPORT

This invention was made with government support under contract No. 5R01CA083831 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 25, 2015, is named K1262.10046US02_SL.txt and is 5,379 bytes in size.

BACKGROUND

It is often difficult to deliver compounds, such as proteins, peptides, nucleic acids and other drugs and diagnostic compounds intracellularly because cell membranes resist the passage of these compounds. It is even more difficult to target a specific type of cell for selective delivery of the compounds.

One method for transmembrane delivery of exogenous molecules is based on the mechanism of receptor-mediated endocytosis (RME). RME is a major mechanism of uptake of impermeant molecules by mammalian cells (Conner, S. D.; Schmid, S. L. *Nature* 2003, 422, 37-44). In this process, extracellular ligands bind cell surface receptors that cluster in dynamic regions of cellular plasma membranes. By actively pinching off to form intracellular vesicles, these membrane regions are internalized, encapsulating ligand-receptor complexes in the cytoplasm. These vesicles fuse and form early (primary/sorting) endosomes that are acidified (pH ~6) by the activation of proton pumps, conditions that generally promote the dissociation of receptors from bound ligands. Free receptors often cycle back to the cell surface, generally via subsequent trafficking through related recycling endosomes (also termed the endocytic recycling compartment) (Maxfield, F. R.; McGraw, T. E. *Nat. Rev. Mol. Cell. Biol.* 2004, 5, 121-132). In contrast, free ligands are typically directed to more acidic late endosomes and lysosomes (pH 5), where hydrolases and other enzymes promote their degradation. Some viruses and other intracellular pathogens exploit RME to enter cells, but these organisms avoid degradation in lysosomes by expressing pH-dependent fusogenic proteins that disrupt endosomal membranes (Lakadamyali, M.; Rust, M. J.; Zhuang, X. *Microbes Infect.* 2004, 6, 929-836). To escape entrapment within these membranes and gain access to the cytosol, Semliki Forest virus disrupts early endosomes whereas influenza virus disrupts late endosomes during the course of infection. Nevertheless, many exogenous molecules that are introduced into cells using RME are not able to escape degradation in the late endosomes or the lysosome. Accordingly, endosomal disruption can facilitate delivery from the endosome into the cytosol of the cell.

Therefore, it would be advantageous to have a compound delivery platform that specifically targeted select cells and enabled endosomal escape to allow the compound to be received into cytosol of a specifically targeted cell.

SUMMARY

In one embodiment, a dual platform delivery system for targeting a cell can include: a first delivery platform having a first targeting moiety linked to an endosome disrupting moiety through a first linker; and a second delivery platform having a different second targeting moiety linked to a cargo agent through a second linker, the second delivery platform being separate from the first delivery platform, wherein the delivery system is configured so as to cause endocytosis of the first delivery platform and second delivery platform in a common endosome, destabilize the endosome, and release the cargo agent from the destabilized endosome into cytosol of the cell.

In one embodiment, the delivery system can include: the first delivery platform including the first targeting moiety as a first receptor targeting moiety; and the second delivery platform including the second targeting moiety as a different second receptor targeting moiety.

In one embodiment, the delivery system can include: the first delivery platform including the first targeting moiety as a first membrane binding element; or the second delivery platform including the second targeting moiety as a second membrane binding element.

In one embodiment, the delivery system can include: at least one of the first targeting moiety or second targeting moiety being a receptor targeting moiety.

In one embodiment, the delivery system can include: the first targeting moiety and second targeting moiety each being configured to associate with different features on the same cell so as to induce endocytosis of the first and second delivery platforms into the same endosome. The different features can be different receptors, different proteins, different polysaccharides, cell membrane, fatty substance or any combination of a receptor, protein, polysaccharide, fatty substance, and a cell membrane In one embodiment, the delivery system can include: the first targeting moiety and second targeting moiety each being configured to associate with different features on the same cell so as to induce endocytosis of the first and second delivery platforms into the same endosome, wherein at least one of the first targeting moiety or second targeting moiety targets a specific receptor on the cell.

In one embodiment, the delivery system can include: the first targeting moiety and second targeting moiety each being configured to associate with different features on the same cell so as to induce endocytosis of the first and second delivery platforms into the same endosome, wherein one of the first targeting moiety or second targeting moiety targets a specific receptor on the cell and the other targets a non-specific feature on the cell.

In one embodiment, the delivery system can include: the first targeting moiety and second targeting moiety each being configured to associate with different features on the same cell so as to induce endocytosis of the first and second delivery platforms into the same endosome, wherein the first targeting moiety targets a first specific receptor on the cell and the second targeting moiety targets a different second specific receptor on the cell, wherein the combination of the first specific receptor and different second specific receptor are selective for targeting a specific type of cell.

In one embodiment, the delivery system can include at least one of the first targeting moiety or second targeting moiety being an antibody or binding fragment thereof.

In one embodiment, the delivery system can include at least one of the first targeting moiety or second targeting moiety being an aptamer targeting moiety.

In one embodiment, the delivery system can include: at least one of the first targeting moiety or second targeting moiety being a small molecule targeting moiety.

In one embodiment, the delivery system can include both the first targeting moiety and second targeting moiety being different antibodies or binding fragments thereof.

In one embodiment, the delivery system can include both the first targeting moiety and second targeting moiety being different aptamer targeting moieties.

In one embodiment, the delivery system can include: both the first targeting moiety and second targeting moiety being different small molecule targeting moieties.

In one embodiment, the delivery system can include only one of the first targeting moiety or second targeting moiety being a membrane binding moiety.

In one embodiment, the delivery system can include the second linker having a region that is selectively cleavable.

In one embodiment, the delivery system can include the first linker having a region that is stable in an endosome.

In one embodiment, the delivery system can include the endosome disrupting moiety being a polypeptide.

In one embodiment, the delivery system can include the cargo agent being selected from the group consisting of cytotoxins, drugs, prodrugs, molecular probes, polypeptides, proteins, polynucleotides, DNA, RNA, siRNA, PNA, morpholinos, carbohydrates, or lipids, and combinations thereof.

In one embodiment, a method of delivering a cargo agent into cytosol of a cell can include: providing the delivery system of one of the embodiments described herein having the first and second delivery platforms; and administering the delivery system to a cell so as to cause targeting of two features on the cell so as to: cause endocytosis of the first and second delivery platforms of the delivery system into a common endosome, destabilize the endosome of the cell having the delivery system, release the cargo agent from the second linker; and release the cargo agent from the destabilized endosome into cytosol of the cell. In one aspect, the first and second delivery platforms are specific for targeting a specific cell type.

In one embodiment, a method of treating a disease can include: performing the method of method of delivering a cargo agent into cytosol of a cell in a subject having a disease, wherein the cargo agent is a therapeutic agent for the disease. As such, both platforms are received into an endosome of a common cell, and the cargo agent, which is a therapeutic, is released into cytosol of the cell. This allows specified on-targeting of cytosol of a cell, and it inhibits off-targeting to other cells.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 6B discloses SEQ ID NO: 17.

DETAILED DESCRIPTION

Figure 1A:
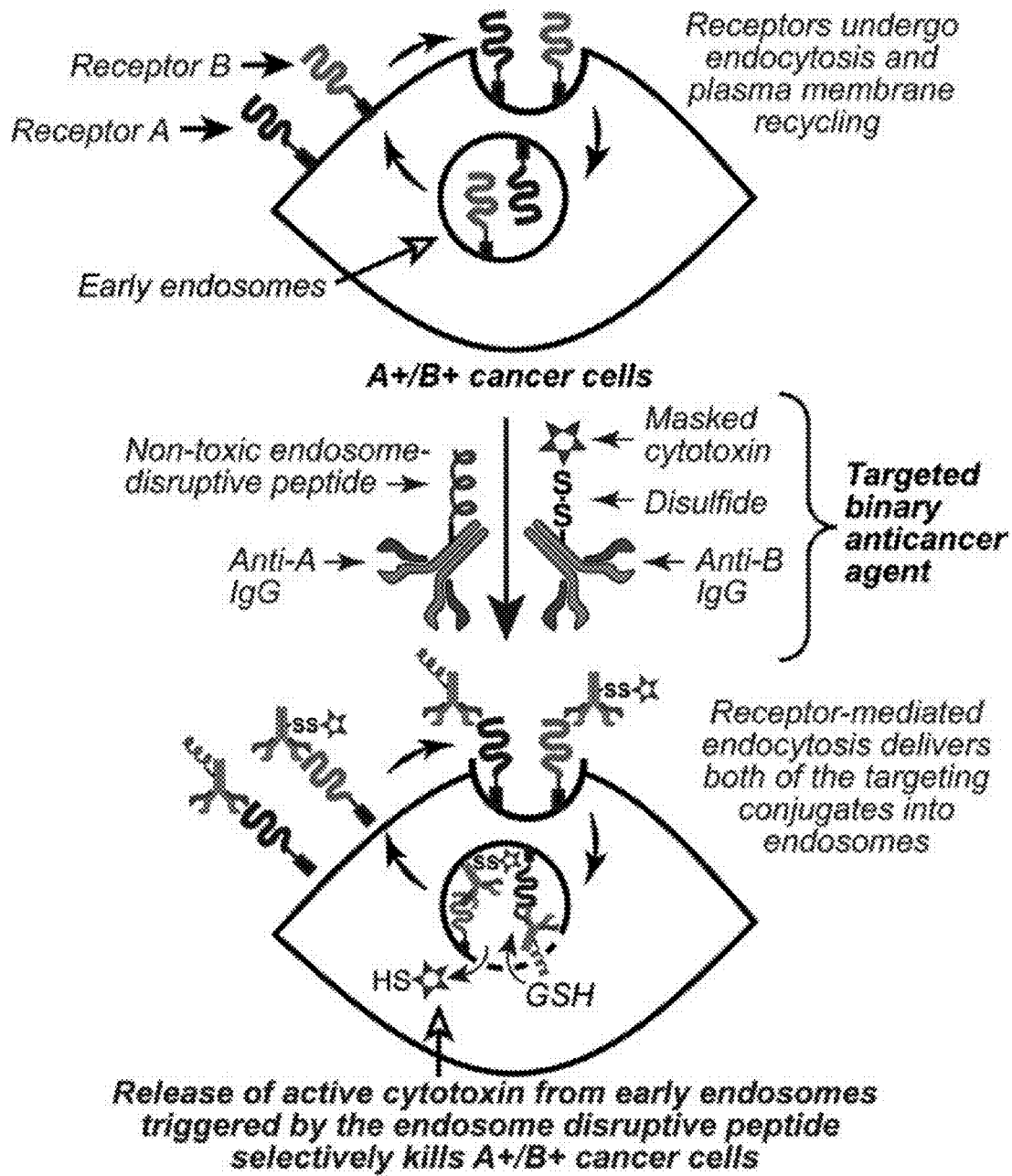
FIG. 1A illustrates a biological pathway for the use of two antibody conjugates for synergistic targeting, also termed here synthetic lethal targeting, of two distinct cell surface receptors (A and B) expressed on cancer cells. The antibodies could be substituted with other targeting proteins, peptides, nucleic acids, small molecules, or ligands that bind internalizing cell surface receptors.
Figure 1B:
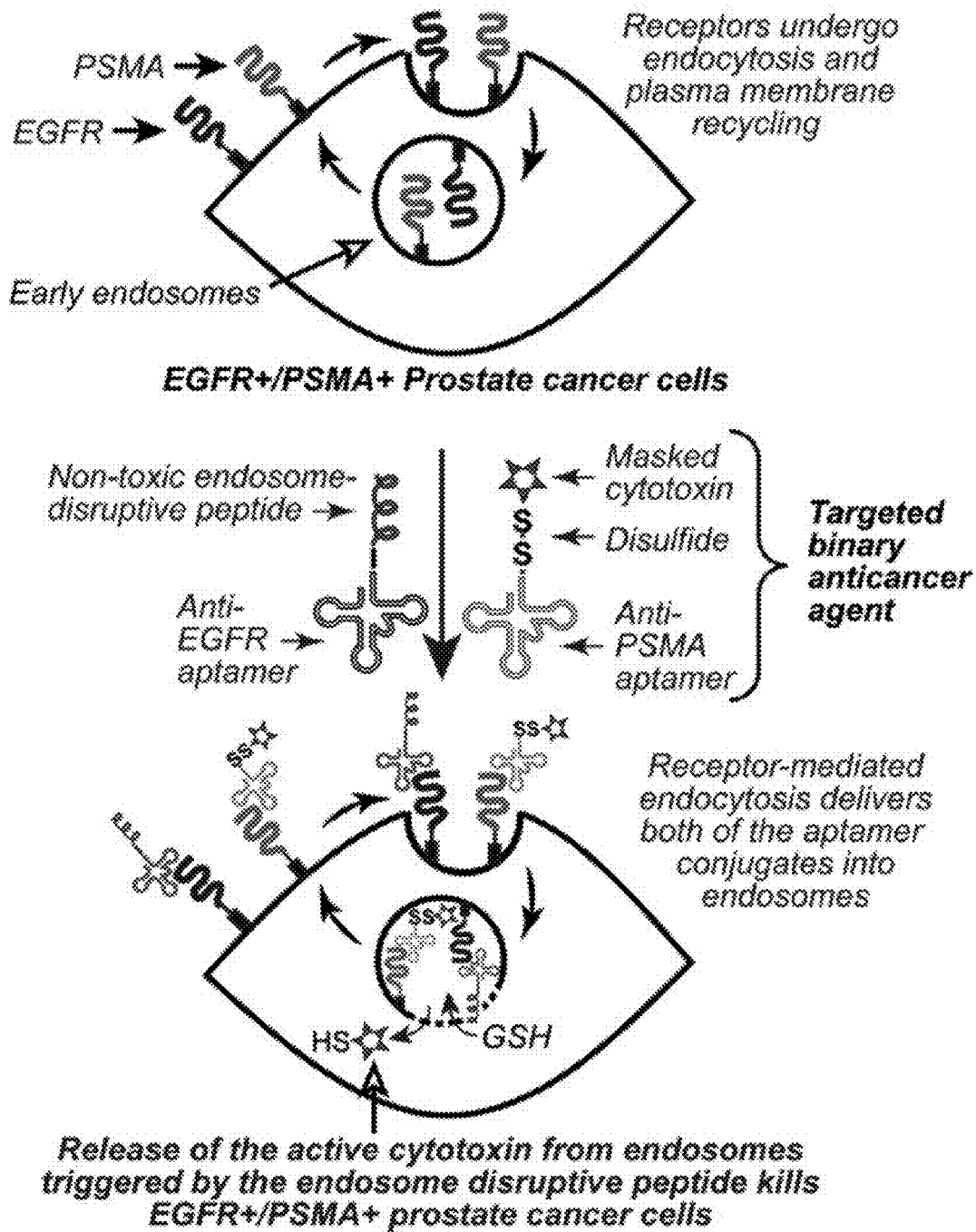
FIG. 1B. illustrates a biological pathway for the use of binary anticancer agents (e.g., two separate agents with different targeting moieties) targeting PSMA and EGFR expressed by some prostate cancer cells.
Figure 2:
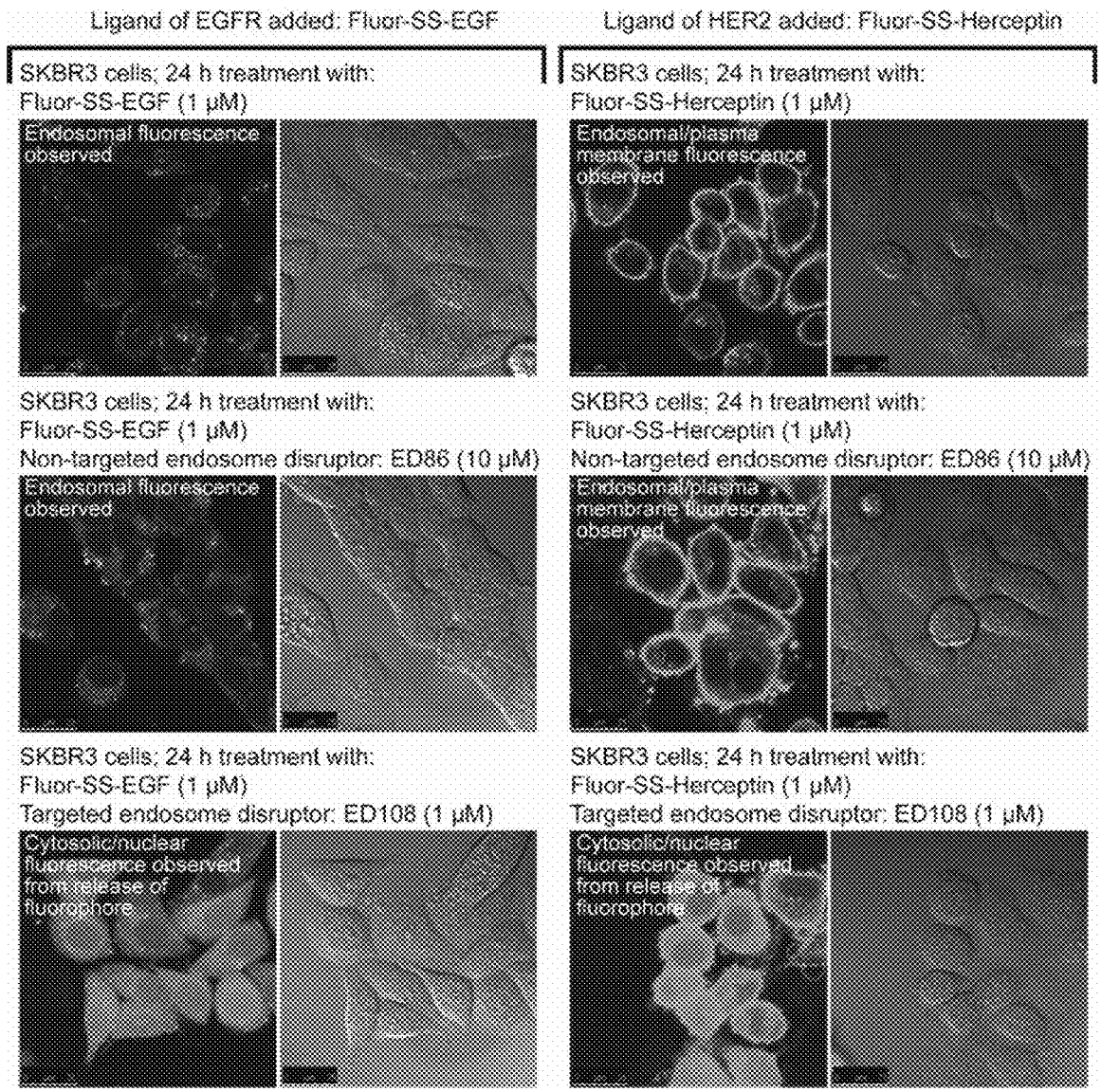
FIG. 2 shows images of confocal (left panels) and DIC (right panels) micrographs showing release of a disulfide-linked fluorophore from the antibody Herceptin into the cytoplasm of SKBR3 breast cancer cells mediated by a targeted cholesterol-conjugated endosome disruptive peptide.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Tumor-targeted anticancer drug conjugates can exhibit therapeutic efficacy against cancers that selectively overexpress a targeted receptor. Yet, even when a specific cell surface receptor is highly overexpressed by cancer cells, some normal cells and tissues frequently also express the same receptor to some extent. This off-target expression can limit the ability of these agents to eradicate all cancer cells without toxic side effects. Synthetic lethal targeting of cells that express two different receptors using the methods disclosed here that utilize two different entities with different receptors can improve selectivity of agents against diseases, such as cancer. Correspondingly, normal cell types, including those that express one of the two targeted proteins, would be less affected by these types of delivery systems. The dual receptor targeting systems of the invention provide increased cell targeting specificity and synergistic delivery of the cargo agent to the cells that express both receptors that are targeted by the dual receptor targeting systems. The dual receptor targeting systems provide low toxicity, high specificity, and novel mechanism of action for delivery of cargo agents into cells as described herein. The dual receptor targeting systems can target any type of cell that preferentially expresses two receptors that are not both present on other cells, which allows for increased on-targeting.

Synthetic lethality is a strategy for drug discovery that shows great promise for specific targeting of cancer cells, as well as other types of cells that express particular receptor combinations. This concept is applied here to targeting of two distinct cell surface receptors, and can be applied to therapies for cancer and other diseases that have cells that express a unique combination of two receptors. The approach is based on the synthesis of two unique compounds that act synergistically when combined in endosomes of mammalian cells. One of these compounds can include a disulfide linker that is attached to cargo such as cytotoxins, drugs, or fluorescent probes. When this cargo is delivered into endosomes, the stability of the disulfide bond, and entrapment in these membrane-sealed compartments, prevents its escape into the cytoplasm. However, addition of a second compound, comprising a membrane-active but non-toxic peptide or other endosome disruptive agent, weakens membranes of these endosomes, enabling cleavage of the disulfide bond and release of the trapped cargo into the cytoplasm and nucleus. It has been demonstrated that when the tubulin-binding cytotoxin colchinol is used as cargo, the combination of these two agents (e.g., cargo and endosome disruptor) enhances lethality to some cancer cell lines by 100-fold or more. It has been demonstrated that cargo conjugated to ligands of cell surface receptors, such as receptor-binding antibodies and other proteins via a disulfide, can be released by coadministration with targeted endosome disruptive peptides, providing proof of concept for synthetic lethal targeting of two different receptors on a single cell surface. This strategy may enhance the specificity of targeted drug conjugates for treatment of cancer and other diseases.

It has been found that synergistic cytotoxic effects can be achieved by delivery of a cholesterol-linked cytotoxin (e.g., colchinol) and cholesterol-linked endosome disruptive peptide in cancer cells. These cholesterol mimics bind an ezetimibe-sensitive cell surface receptor. Now, it has been found that enhanced synergistic effects and specific cell targeting can be obtained when a first delivery platform has a first targeting moiety that targets a first receptor on a cell is combined and delivered with a second delivery platform that has a different second targeting moiety that targets a different second receptor on the cell. When one of the first or second delivery platform has a cargo agent and the other has an endosomal disrupting moiety, the combination of the first and second delivery platforms can target a cell with high specificity and with synergistic effect for delivery of the cargo agent. In one aspect, one or both of the targeting moieties includes one or more aptamers so that the two different targeting moieties target two different cell surface receptors on the same cell surface. For example, one or both of the aptamer targeting moieties can target receptors on prostate cancer cells, and the cargo agent can be a therapeutic for targeted treatment of prostate cancer, and inhibition of proliferation of prostate cancer. The targeting moieties can target PSMA and/or target CD44 and/or EGFR. In one aspect, the dual receptor targeting system can include two different delivery platforms that are configured to include targeting moieties for targeting PSMA and EGFR.

In one embodiment, the present invention includes at least a delivery system with dual platform delivery systems that target dual receptors on a single cell surface. It has been demonstrated that the dual platform delivery system can release disulfide-linked fluorescent probes (e.g., cargo agent, and which can be substituted with any other cargo agent) from the dual platform delivery systems. At least one of the targeting moieties of the dual platform delivery systems can include the anticancer antibody Herceptin (e.g., first targeting moiety) that targets receptors on the HEK 293 cells engineered to overexpress the HER2 receptor. Release was mediated by an endosome disruptive peptide linked to a mimic of cholesterol (e.g., second targeting moiety) that is internalized via an ezetimibe-sensitive cell surface receptor. No release of the fluorescent probe was observed with an endosome disruptive peptide lacking the receptor-binding cholesterol mimic, demonstrating that targeting of two cell surface receptors can result in a synergistic delivery effect when one delivery platform has a cargo moiety and the other has an endosome disrupting moiety.

In one embodiment, the present invention includes a delivery system for targeting two different receptors on a cell so as to cause endocytosis of the delivery system, destabilizing an endosome of the cell having the delivery system, and delivering a cargo agent from the destabilized endosome into cytosol of the cell. Such a delivery system can include: a first delivery platform having a first receptor targeting moiety linked to an endosome disrupting moiety through a first linker; and a second delivery platform having a different second receptor targeting moiety (e.g., the first and second receptor targeting moieties are different) linked to a cargo agent through a second linker. In one aspect, the linkers can have regions that are selectively cleavable. In one aspect, the first and second receptor targeting moieties are configured to target and associate with first and second receptors, respectively, on a cell surface so as to induce endocytosis into a common endosome. In one aspect, the endosome disrupting moiety destabilizes the endosome such that the cargo agent is released from the second targeting moiety and/or second linker or portion thereof and escape the endosome into the cytosol of the cell.

Cells that express two different targeted receptors can be targeted by the two platform system to be killed, whereas cells expressing only one of these receptors would be unharmed. This approach can enhance the selectivity and reduce the off-target toxicity of antibody-drug conjugates (ADCs). One delivery platform combines an antibody that binds to a specific receptor on cell surfaces with a potent cytotoxin that kills cells that bind and internalize the antibody, and the other delivery platform has a different antibody that binds to a different receptor on the same cell and that has an endosome disruptor.

In one embodiment, the dual platform delivery system can be used for targeting and eradication of the cancer stem cells that drive the proliferation of incurable prostate cancers. This duel delivery platform can include two different antibody conjugates that together possess a unique cytotoxic synergy. This synergy is based on the formation of an active cytotoxin that can escape an endosome only when two different antibody conjugates co-accumulate in endosomes of prostate cancer stem cells that uniquely coexpress different receptors, such as the different cell surface proteins CD44 and CD133. The dual platform delivery system can have different platforms that has one platform to target CD44 and one platform to target CD133. This synergistic effect can result from the activation of a cytotoxic warhead on one antibody by a trigger linked to a second antibody in cells that express two different receptors. Correspondingly, the many normal cell types that express only one of these two receptors would be unaffected, allowing dose escalation and complete eradication of prostate cancers It has been demonstrated that release of disulfide-linked fluorescent probes can be obtained from the anticancer antibody Herceptin in HEK 293 cells engineered to overexpress the HER2 receptor. Release was mediated by an endosome disruptive peptide linked to a mimic of cholesterol that is internalized via an ezetimibe-sensitive cell surface receptor. No release of the fluorescent probe was observed with an endosome disruptive peptide lacking the receptor-binding cholesterol mimic, demonstrating that targeting of two cell surface receptors can result in a synergistic delivery effect. While proof of concept uses a receptor targeting moiety and a mimic of cholesterol as a membrane targeting moiety, the invention extends to both delivery platforms having different receptor targeting moieties.

In one embodiment, synergistic targeting of two distinct cell surface receptors by two distinct delivery platforms with different receptor targeting moieties can be used for therapies to treat cancer proliferation and other diseases. This strategy is related to synthetic lethality in that that these two receptors confer a lethal phenotype only when co-targeted by two complementary agents (e.g., the two different delivery platforms with different targeting moieties). This approach is based on the synthesis of two unique compounds that act synergistically when combined in endosomes of mammalian cells.

One of these compounds bears a disulfide linker that is attached to cargo such as cytotoxins, drugs, or fluorescent probes. When this cargo is delivered into endosomes, the stability of the disulfide bond, and entrapment in these membrane-sealed compartments, prevents its escape into the cytoplasm. However, addition of a second compound, comprising a membrane-active but non-toxic peptide or other endosome disruptive agent, alters membranes of these endosomes, enabling cleavage of the disulfide bond and release of the trapped cargo into the cytoplasm and nucleus. To provide evidence in support of this concept, we demonstrated that when the tubulin-binding cytotoxin colchinol is used as cargo, and cholesterol mimics are used as cellular targeting elements, the combination of these two agents can enhance lethality to cancer cell lines by 100-fold or more. We have demonstrated that cargo conjugated to ligands of cell surface receptors such as receptor-binding antibodies and other proteins via a disulfide can be released by coadministration with targeted endosome disruptive peptides, providing further proof of concept of synthetic lethal targeting. This strategy is designed to enhance the specificity of targeted drug conjugates for treatment of cancer and other diseases.

Antibodies and growth factors can be linked to cargo via disulfides and the cargo can be released by cholesterol-linked endosome disruptive peptides. In this case, the antibody, growth factor, or cholesterol moiety represents the targeting group. Based on these results, an endosome disruptive peptide could be similarly linked to antibodies, growth factors, or other ligands of internalizing biomolecules on the cell surface to provide agents for synthetic lethal targeting.

FIG. 1A illustrates the principle of synthetic lethal targeting using two antibodies where one antibody is conjugated to a cytotoxin via a disulfide and the second antibody is conjugated to an endosome disruptive peptide, either alone or via a cleavable linker, such as a linker sensitive to proteolysis. Accordingly, FIG. 1A illustrates a biological pathway for the use of two antibody conjugates for synthetic lethal targeting of two distinct cell surface receptors (A and B) expressed on cancer cells. The antibodies could be substituted with other targeting proteins, peptides, nucleic acids, small molecules, or ligands that bind internalizing cell surface receptors. FIG. 1B illustrates that other receptor targeting moieties, such as aptamers, can be used to target two different receptors on the same surface. However, it should be recognized that a the two different delivery platforms can have different types of receptor targeting moieties and/or cell targeting moieties, such as combinations of two or more of antibodies, other targeting proteins, peptides, nucleic acids, small molecules, or ligands that bind internalizing cell surface receptors or the cell membrane.

FIG. 2 shows confocal micrographs of SKBR3 breast cancer cells treated with ligands of EGFR and HER2 conjugated to a fluorophore via a disulfide. Panels on the left show cells treated with an EGF conjugate that binds EGFR whereas panels on the right show cells treated with a conjugate of the antibody Herceptin that binds HER2. In the middle panels, a non-targeted endosome disruptive peptide (ED86) was added. In the bottom panels, a targeted cholesterol modified endosome disruptive peptide (ED108) was added. Release of the fluorophore from EGF or Herceptin into the cytosol and nucleus was observed upon co-administration of the targeted endosome disruptive peptide. In conjunction with our previous studies of disulfide-linked colchinol conjugates (see provisional application), these studies provide evidence that targeting of two distinct cell surface entities (e.g., two receptors or a receptor and membrane) with a cytotoxic conjugate and an endosome disruptive peptide can confer a synthetic lethal-type effect against cancer cell lines. This shows that targeting two different cell surface receptors may be even more specific for enhanced on-targeting and reduced off-targeting.

Accordingly, FIG. 2 shows confocal (left panels) and DIC (right panels) micrographs showing release of a disulfide-linked fluorophore from the antibody Herceptin into the cytoplasm of SKBR3 breast cancer cells mediated by a targeted cholesterol-conjugated endosome disruptive peptide (ED108, sequence: Cholesterol carbamate-(βAla)$_2$-(Glu)$_2$-mPEG-(βAla)$_4$-(Aib)$_4$-(Trp)$_2$-Ala-Trp-Tyr-(Pro)$_2$-Val-Val-CONH2 (SEQ ID NO: 2)). In this cell line, release was not observed with a related endosome disruptive peptide lacking the cellular-targeting cholesterol moiety (ED86, sequence: H2N-(Aib)$_4$-(Trp)$_2$-Ala-Trp-Tyr-(Pro)$_2$-Val-Val-CONH2 (SEQ ID NO: 3)), despite addition of a 10-fold higher concentration of this compound (middle panels).

A wide variety of internalizing cell surface receptors could be targeted in this way. These receptors include but are not limited to growth factor receptors, death receptors, receptors for nutrients such as folate, vitamins, peptides, proteins, and lipoproteins, other nutrient receptors, orphan receptors, and other receptors in these and other families. Examples include but are not limited to EGFR, HER2, HER3, CD44, CD133, CD30, PSMA, PDGFR, TFR, LDLR, and FOLR. The combination of two different receptors on a single cell surface allows for enhanced specificity for delivering a cargo into cytoplasm.

Figure 3:
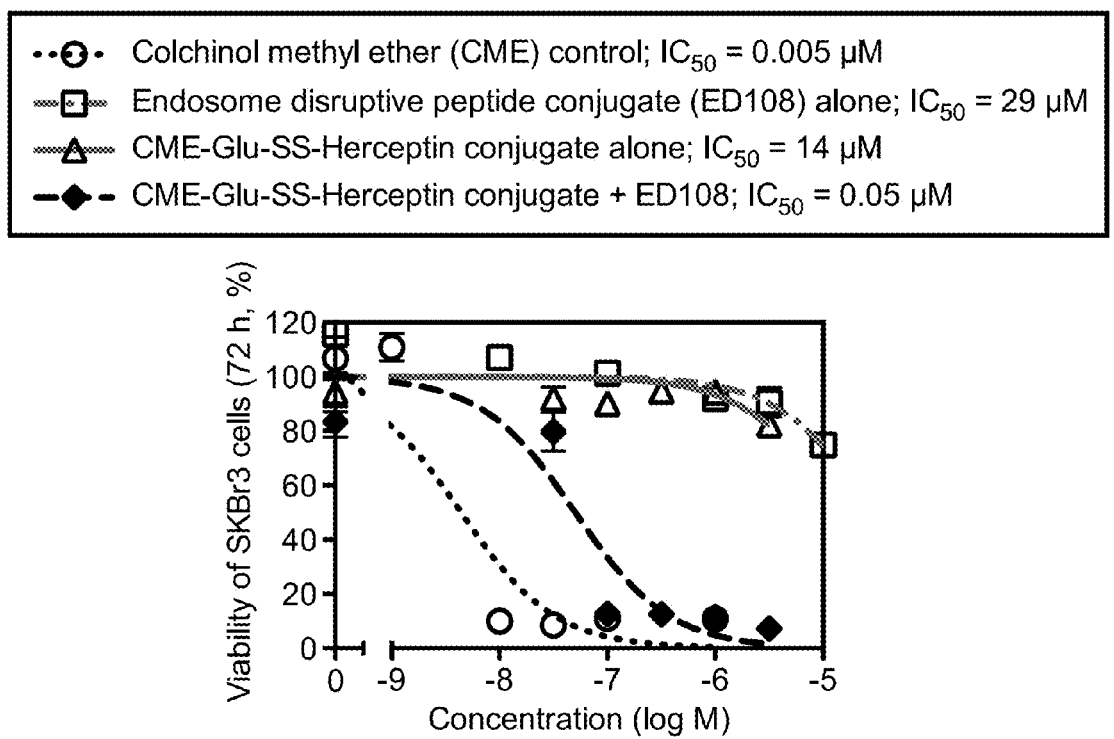
FIG. 3 shows a graph that illustrates the effect of the cytotoxin colchinol methyl ether (CME), Herceptin conjugated to this cytotoxin via a disulfide, and the targeted endosome disruptor ED108 (e.g., endosome disruptive peptide linked to a cholesterol moiety) on SKBr3 breast cancer cells. Cellular viability was analyzed by flow cytometry after 72 h. Addition of ED108 to the antibody conjugate synergistically enhances cytotoxicity.

FIG. 3 shows the viability of SKBr3 breast cancer cells treated for 72 hours with the antibody Herceptin conjugated to the cytotoxin colchinol methyl ether via a disulfide. This data with an antibody-cytotoxin conjugate demonstrates that the endosome disruptive agent ED108 can be used to synergistically enhance cytotoxicity. Accordingly, FIG. 3 shows the effect of the cytotoxin colchinol methyl ether (CME), Herceptin conjugated to this cytotoxin via a disulfide, and the targeted endosome disruptor ED108 on SKBr3 breast cancer cells. Cellular viability was analyzed by flow cytometry after 72 h. Addition of ED108 (e.g., cholesterol mimic targeting moiety linked to endosome disruptor) to the antibody conjugate synergistically enhances cytotoxicity.

In one embodiment, the two unique compounds can be configured to act synergistically when combined in endosomes of cancer cells. One of these compounds includes a disulfide linker that is attached to cargo such as cytotoxins or fluorescent probes. This cargo becomes trapped in endosomes when delivered into these compartments, rendering it inert when alone. However, addition of a second compound that comprises a short membrane-lytic but non-toxic peptide disrupts endosomes to release this cargo from these compartments.

In one embodiment, the targeted binary agents exhibit a unique synergy: their combination can form an active cytotoxin only in cells that express two different cell surface receptors. By avoiding toxicity to normal cells that express only one of two targeted antigens, this approach has the potential to amplify the level of selectivity achievable by targeted anticancer agents. To evaluate this hypothesis, one delivery platform can target Prostate Specific Membrane Antigen (PSMA) and the other delivery platform can target Epidermal Growth Factor Receptor (EGFR). These are two different receptors that can be overexpressed in metastatic prostate cancer, but that do not appear to be simultaneously co-expressed at high levels in normal cell types.

PSMA is overexpressed by almost all prostate cancers, with the highest levels of expression in metastatic and hormone-refractory prostate cancer cells. However, PSMA is also known to be expressed in some normal tissues including the normal prostate, normal kidney, normal bladder, normal small intestine and normal salivary glands. This expression by off-target tissues can limit the potential of delivery systems focused solely on targeting PSMA in prostate cancer. Additionally, the growth-promoting EGFR is also frequently expressed in aggressive metastatic cancers. This receptor is associated with the transition of prostate cancer from an androgen-responsive and treatable form to the incurable androgen-independent phenotype. In addition to metastatic prostate cancer cells, the EGFR is expressed in other cell types including the epidermis, where EGFR critically maintains the epidermal phenotype. Consequently treatment with EGFR inhibitors can be associated with cutaneous toxicity, and agents that solely target the EGFR for therapeutic delivery in prostate cancer may suffer from these effects as well. The dual platform delivery system can improve the selectivity of molecularly targeted therapeutics by being designed to only kill prostate cancer cells that express both PSMA and EGFR. This concept can be extrapolated to any other disease with cells having two receptors that the combination thereof is unique to the targeted disease cell.

In one embodiment, the dual platform delivery system includes two molecular entities that are lethal only when combined in a cell expressing two different receptors. These binary chemical agents are based on the discovery that specific hydrophobic peptides can alter the oxidation potential of early endosomes of mammalian cells while exhibiting low toxicity. This change in oxidation potential can be used to release disulfide-linked cargo from the same endosomal compartment into the cytoplasm. A disulfide-linked derivative of colchinol, which is a cytotoxic antitubulin agent, was delivered into endosomes of PC3 prostate cancer cells by conjugation to a mimic of cholesterol. This masked cytotoxin is of low toxicity when administered alone, because the specific disulfide-linked conjugate is highly stable in the oxidizing environment of the lumen of early/recycling endosomes. However, when a similarly non-toxic endosome disruptive peptide is co-administered, this peptide forms small pores in membranes of these endosomal compartments, allowing reduction of the disulfide bond, and release of the cytotoxin into the cytoplasm, resulting in death of the cancer cell. Thus, this approach can be used to create binary agents targeting both PSMA and EGFR found on metastatic prostate cancer cells. When these internalizing receptors cycle between the cell surface and early/recycling endosomes, molecules that bind these receptors will be released and accumulate in endosomes. By linking endosome disruptive peptides to a first targeting moiety (e.g., antibodies or nucleic acid aptamers) with high affinity for EGFR, and by linking cytotoxins to a second targeting moiety (e.g., antibodies or aptamers) that target PSMA, compounds are obtained that are individually non-toxic; yet, when mixed in early endosomes upon endocytosis, kill PSMA+/EGFR+ prostate cancer cells with high selectivity.

Aptamers, nucleic acid-based affinity agents, represent a powerful yet simple approach for targeting cells. These affinity reagents typically bind targets with nanomolar or better affinities and have specificities comparable to monoclonal antibodies. However, unlike antibodies, aptamers are smaller, more chemically-defined, and can be prepared by chemical synthesis, facilitating downstream conjugation to drugs and peptides such as the cytotoxins and endosome disruptors proposed here. In vivo, aptamers can be safe, non-immunogenic, and efficacious.

Aptamers are generated by iterative rounds of in vitro selection. Briefly, randomized pools of RNA or ssDNA are incubated with target molecules under carefully chosen selection conditions. Binding species are partitioned away from non-binders, amplified to generate a new pool, and the process is repeated until a desired 'phenotype' is achieved or until sequence diversity is significantly diminished. Multiple cycles of selection and amplification tend to winnow a pool of upwards of $10^{15}$ molecules to only those few species that have the highest affinities and specificities for a target. Whereas aptamers have traditionally been generated against soluble proteins or small molecule targets, aptamer selection techniques have more recently expanded to include cell surface targets, whole cells, and even in vivo selection procedures. Some aptamers selected against specific cell surface receptors have been successfully used for the delivery of cargoes into cells and are being investigated for in vivo targeting and delivery. Aptamers targeting PSMA can be linked to cargo, such as ribosomal toxin gelonin.

Aptamers that can be used at targeting moieties are provided in Table 1 below. Table 1 discloses SEQ ID NOS 4-16, respectively, in order of appearance.

(Panel D) shows some co-localization (yellow) in endosomes as indicated by white arrows. The binary agents are designed to selectively kill PSMA+/EGFR+ prostate cancer cells through the mechanism proposed here both accumulate in common endosomal compartments.

Over the past decade, an overwhelming abundance of evidence indicates a small subpopulation of cancer stem cells (CSCs) is present in a wide range of tumor types. CSCs actively replicate, and they initiate tumor proliferation, self-propagation, and differentiation into all the phenotypically diverse cells of the tumor population. Moreover, CSCs are more resistant to chemotherapy and radiation than other cancer cells, making complete eradication of cancer during therapy a challenge. The presence of CSCs in solid tumors provides an explanation for the phenomenon of drug-refrac-

TABLE 1

| Aptamer | Target | Type | Sequence |
|---|---|---|---|
| A9min | PSMA | 2'F RNA | 5'-GGGACCGAAAAAGACCUGACUUCUAUACUAAGUCUACGUUCCC-3' |
| A10-3 | PSMA | 2'F RNA | 5'-GGGAGGACGAUGCGGAUCAGCCAUGUUUACGUCACUCCUUGUCAAUCCUCAUCGGC-3' |
| A10-3.2 | PSMA | 2'F RNA | 5'-GGGAGGACGAUGCGGAUCAGCCAUGUUUACGUCACUCCU-3' |
| C2 | hTfR | 2'F RNA | 5'-GGGGGAUCAAUCCAAGGGACCCGGAAACGCUCCCUUACACCCCT-3' |
| E07.min | EGFR | 2'F RNA | 5'-GGACGGAUUUAAUCGCCGUAGAAAGCAUGUCAAAGCCGGAACCGUCC-3' |
| CL4 | EGFR | 2'F RNA | 5'-GCCUUAGUAACGUGCUUUGAUGUCGAUUCGACAGGAGGC-3' |
| XEO2-mini | PC3 cells | 2'OMethyl ACU, | 5'-CACGACGCUGAUGGAUCGUUACGACUAGCAUCGC-3' |
| EpCAM | EpCAM | 2'F RNA | 5'-GCGACUGGUUACCCGGUCG-3' |
| AS1411 | Nucleolin | DNA | 5'-TTGGTGGTGGTGGTTGTGGTGGTGGTGG-3' |
| Sgc8c | PTK7 | DNA | 5'-ATCTAACTGCTGCGCCGCCGGGAAAATACTGTACGGTTAGA-3' |
| 2-2 | HER2 | DNA | 5'-GCAGCGGTGTGGGGGCAGCGGTGTGGGGGCAGCGGTGTGGGG-3' |
| Her2.mini | HER2 | 2'F RNA | 5'-AGCCGCGAGGGGAGGGAUAGGGUAGGGCGCGGCU-3' |
| WAZ | hTfR | 2'F RNA | 5'-GGGUUCUACGAUAAACGGUUAAUGAUCAGCUUAUGGCUGGCAGUUCCC-3' |

Aptamers that bind PSMA and EGFR colocalize in endosomes of PC3 prostate cancer cells. To create targeted binary cytotoxins that selectively kill PSMA+/EGFR+ prostate cancer cells, the agents both accumulate in the same endosomal compartments. To examine whether aptamers targeting PSMA and EGFR would colocalize in endosomes of PC3 cells expressing PSMA (PC3-PSMA), the green fluorophore AF488 was conjugated to the PSMA-binding aptamer A9 and the red fluorophore DY650 to the EGFR-binding aptamer E07. Confocal microscopy and flow cytometry revealed that both of these aptamers are internalized by PC3-PSMA cells; when combined, they also colocalize in endosomes. This result supports the hypothesis that when these aptamers are individually linked to endosome disruptive peptides and disulfide-linked cytotoxins, synergistic cytotoxic effects will be observed.

Figure 4:
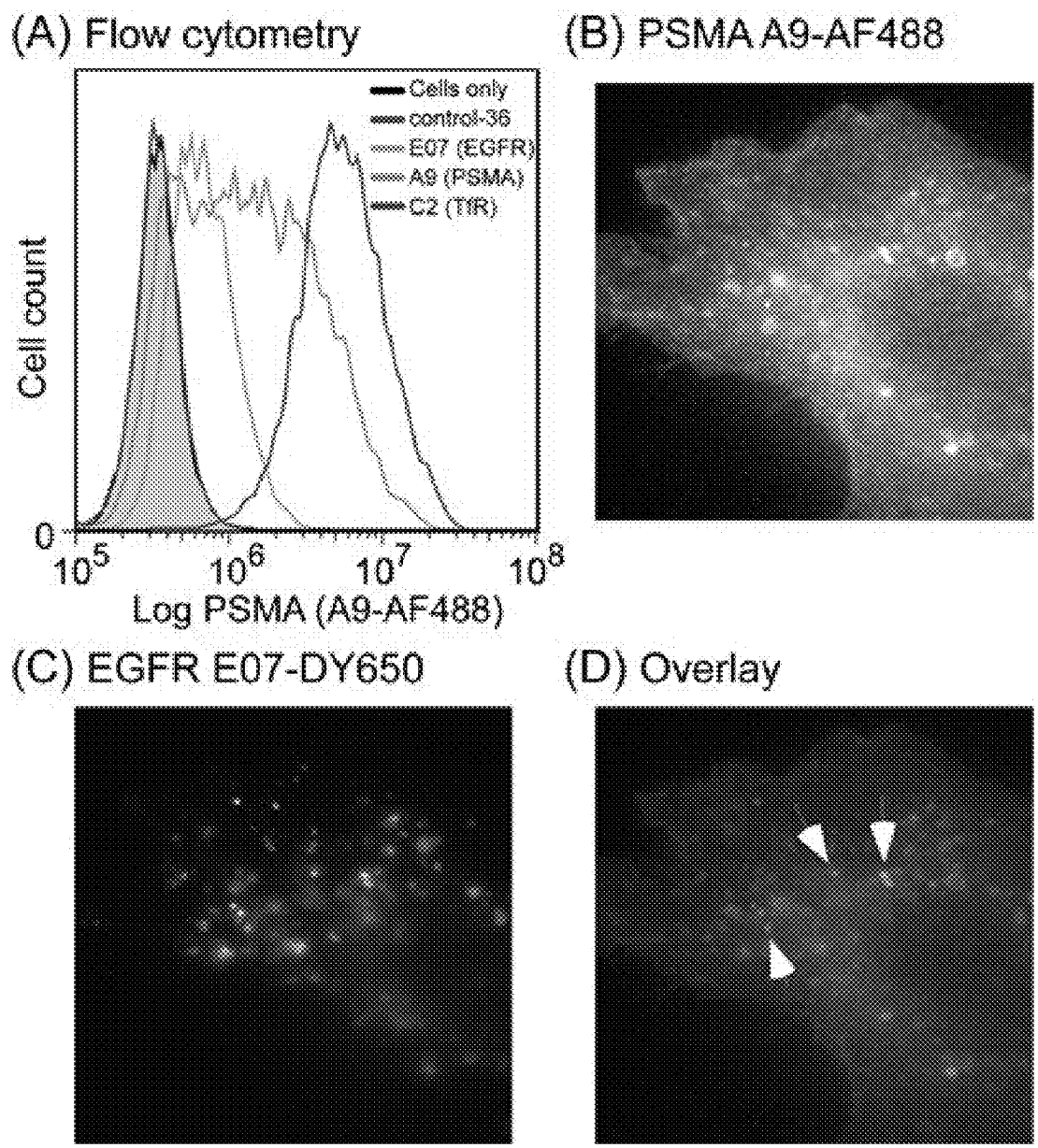
FIG. 4 includes panels A, B, C, and D, which show binding, uptake and co-localization of aptamers by cells: Panel A shows analysis of PC3-PSMA cells by flow cytometry after incubation with 100 nM Dy650-labeled anti-PSMA (A9), anti-hTfR (c2) and anti-EGFR (E07) aptamers or a non-functional aptamer control (control-36); Panels B-D include fluorescence micrographs of AF488-labeled anti-PSMA apamer (Panel B) and a Dy650-labeled anti-EGFR aptamer (Panel C) following co-incubation with PC3-PSMA cells for 1 h; and an overlay of the images (Panel D) shows some co-localization (arrows pointing to endosomes) in endosomes as indicated by white arrows.

FIG. 4 shows data for binding, uptake and co-localization of aptamers by cells. Panel A shows analysis of PC3-PSMA cells by flow cytometry after incubation with 100 nM Dy650-labeled anti-PSMA (A9), anti-hTfR (c2) and anti-EGFR (E07) aptamers or a non-functional aptamer control (control-36). Panels B-D show fluorescence micrographs of AF488-labled anti-PSMA apamer (Panel B) and a Dy650-labeled anti-EGFR aptamer (Panel C) following co-incubation with PC3-PSMA cells for 1 h. Overlay of the images tory relapse, one of the most difficult problems in treating cancer patients. Consequently, new approaches to target these cells and prevent the emergence of drug resistance are urgently needed.

It has been found that proteins CD44 and CD133 can be markers of cancer stem cells that drive the proliferation of prostate cancers. Therefore, targeting moieties that target CD44 and CD133 can be used in the dual platform delivery system.

CD44 is a highly glycosylated cell surface receptor of ~90 KDa involved in cellular adhesion, proliferation, apoptosis, cellular migration, metastasis, and chemo-resistance, among other functions. This receptor predominantly binds hyaluronic acid but also interacts with other ligands including osteopontin, serglycin, collagens, fibronectin, and laminin. CD44 is widely known to be expressed by CSCs that drive the proliferation of a number of solid cancers, including prostate cancer. Prostate cancer stem cells express low levels of androgen receptors, and self-renewing CD44+ cells, comprising 0.1% of the total prostate tumor cells, have been isolated from primary prostate cancers. These CSCs have significant clinical implications because they exhibit greater resistance to chemotherapy and radiotherapy than other cancer cells. In normal tissues, CD44 is also expressed by embryonic cells, hematopoietic progenitor cells, and mature blood cells. As a result of this pattern of expression, an antibody-drug conjugate comprising anti-CD44 linked to the toxin mertansine was previously shown to exhibit severe dose-limiting skin toxicity and was discontinued from clinical trials. Consequently, expression of this protein by off-target tissues limits the potential of cytotoxic delivery systems focused solely on targeting CD44 in prostate cancer.

CD133 is a member of the pentaspan/prominin family of proteins. This cell surface protein of ~120 KDa is highly glycosylated and spans the plasma membrane five times. The function of CD133 not well understood, but it has been proposed to be involved in the organization of the plasma membrane. This receptor is considered a confirmed marker of cancer stem cells, including prostate cancer stem cells, and its expression correlates with low survival in colon cancer. In preclinical studies, the anti-CD133 antibody AC133 was previously conjugated to the cytotoxin monomethyl auristatin via a protease sensitive linker. This immunoconjugate was shown to be internalized in Hep3B hepatocellular cancer cells, possess a targeted cytotoxic effect, and delay tumor growth in vivo. However, CD133 is also expressed by normal haematopoietic progenitors, and other normal cell types, suggesting that cytotoxic agents that solely target this receptor will manifest adverse effects.

Approximately 0.1% of prostate cancer cells represent CSCs that express high levels of CD44 and CD133. These cells undergo self-renewal, proliferation, and differentiation in vitro to the original tumor phenotype. Using the strategy of synthetic lethal targeting, antibody conjugates can be generated that that selectively kill CD44+/CD133+ prostate CSCs without harming normal cells that express only one of these two proteins. As an added margin of safety, auristatin conjugates can be used to investigate this approach. These tubulin-binding cytotoxins will only kill actively proliferating and actively self-renewing CSCs, and should not harm normal non-replicating hematopoietic stem cells that also express CD44 and CD133.

Figure 5:
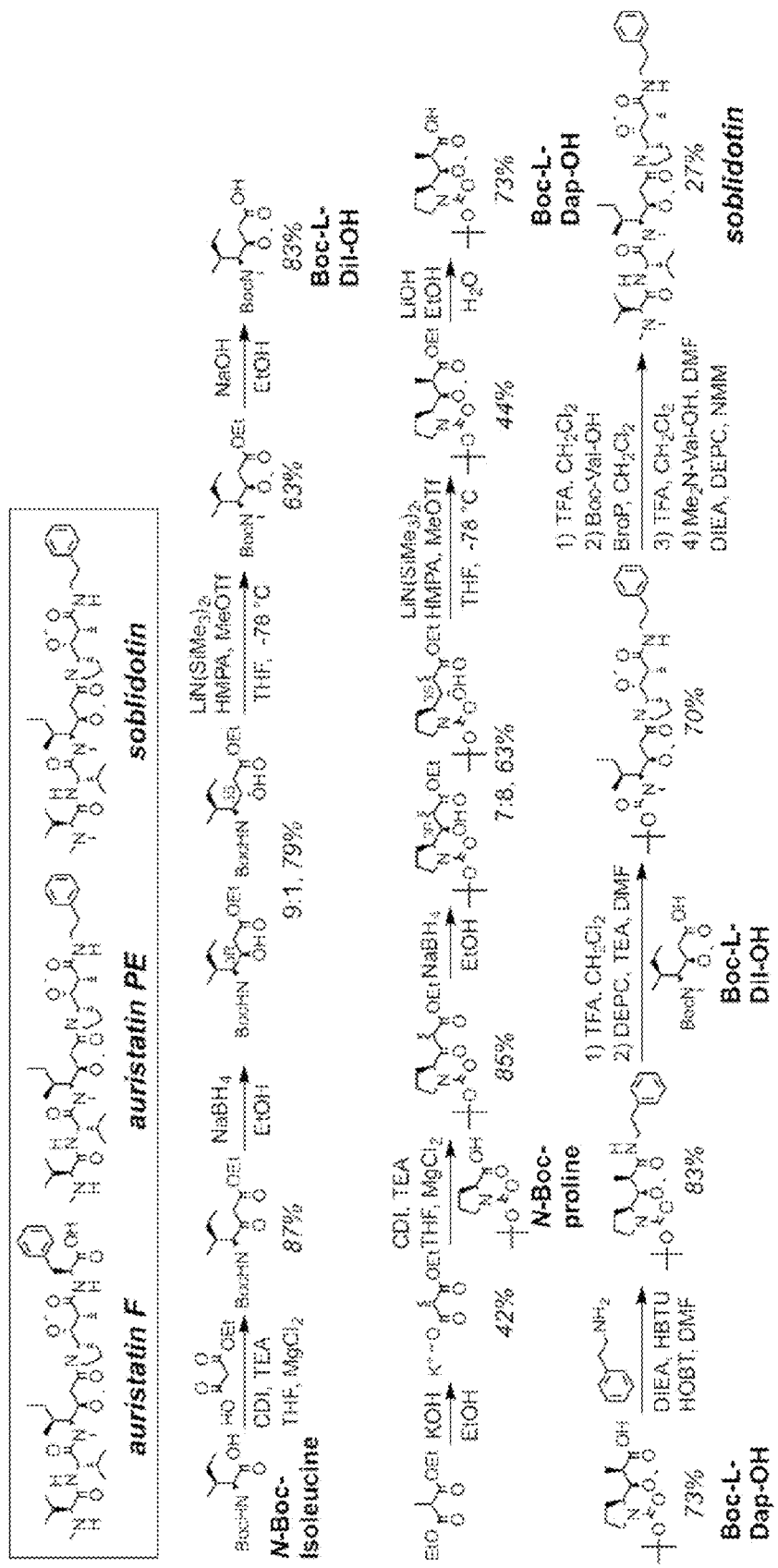
FIG. 5 shows synthesis protocols for delivery platform molecules.
Figure 6:
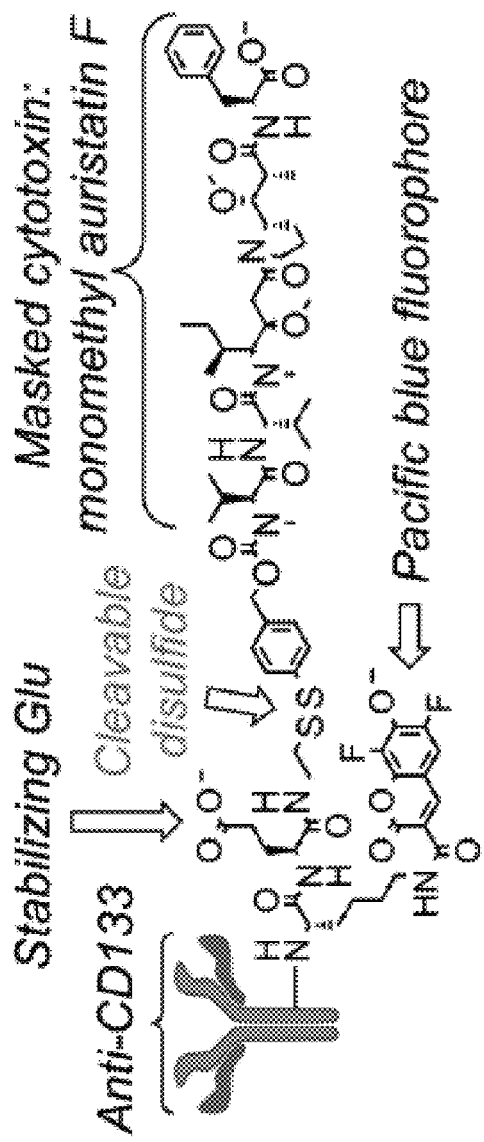
FIG. 6 shows example delivery platform molecules.
Figure 6:
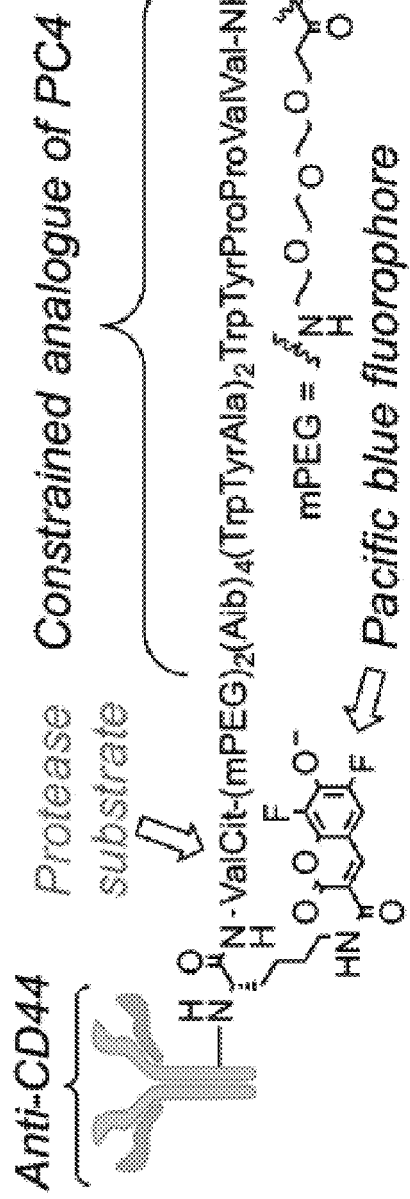

In one embodiment, disulfide derivatives of auristatins including auristatin F and the more potent and hydrophobic auristatin PE (FIG. 5) can be prepared. Using known synthetic methods, as shown in FIG. 5, two key auristatin building blocks, Boc-L-DAP-OH and Boc-L-DiI-OH, have been prepared. The intermediates were used to synthesize the structurally related cytotoxin soblidotin. Disulfide derivatives suitable for antibody conjugation can be linked to antibodies targeting CD44 and CD133, via novel Glu-containing linkers that have been shown to stabilize disulfides in endosomes, to provide compounds such as Compound 14 (FIG. 6). Auristatins were chosen for these studies because monomethyl auristatin E comprises the highly cytotoxic warhead of FDA-approved ADC Adcetris. The auristatins function by potently blocking tubulin polymerization, with $IC_{50}$ values of less than 1 nM, and they are selective against proliferating cells.

The linker between cytotoxins and targeted agents can have a profound effect on the metabolic fate and activity of the cytotoxin. Consequently, a variety of disulfide-containing linkers can be designed to mask the activity of the cytotoxin in the absence of an endosome disruptor. These linkers can include glutamic acid, or related anionic functionality. This glutamic acid, positioned proximal to the disulfide, sharply reduces toxicity in the absence of the endosome disruptor, and is critical for efficient synergy. It is thought that this polar Glu residue may prevent association with protein disulfide isomerase (PDI) enzymatic activity of endosomal membranes that otherwise cleaves the disulfide bond of other more toxic disulfide conjugates. Related disulfide-containing linkers that bear methyl and gem dimethyl substituents alpha to sulfur, which may be necessary to confer high levels of stability in serum in vivo may also be prepared. Many existing disulfide-containing linkers with tunable stability profiles useful for the construction of ADCs have been reported in the literature, and such linkers can be used in the delivery platforms described herein.

Endosome disruptive peptides, such as the constrained analogue of PC4 shown conjugated to anti-CD44 (Compound 15) in FIG. 12, can be synthesized on solid-phase, using known methods, and conjugated to Lys residues of antibodies using NHS ester chemistry as employed in the FDA-approved ADC Kadcyla. It is proposed to incorporate protease cleavage sites such as the Val-Cit dipeptide found in Adcetris to facilitate release of the endosome disruptive peptide in endosomes. This dipeptide is a known substrate of Cathepsin B in endosomes, but is stable in serum in vivo, making it an attractive candidate for incorporation into the linker of endosome disruptive conjugates. Other characterized substrates of cathepsins expressed in endosomes of cancer cells may also be used, since variations in the expression of proteases, and other enzymes in the endolysosomal system, in different cancer cell types can impact the linker required for release of conjugates. As a positive control, auristatin PE linked to anti-CD44 and anti-CD133 using a linker similar to that of Adcetris can be prepared. This will allow comparisons of synergistic binary agents, activated by controlled disruption of endosomes, with a cytotoxic ADC that is activated by proteolysis, while targeting the same receptors under investigation (CD133/CD44). The inclusion of the small anionic Pacific Blue fluorophore in the linker of these compounds can facilitate determination of the drug-antibody ratio, and further allow quantification of cellular binding, uptake, and other mechanistic studies by confocal microscopy and flow cytometry.

In one embodiment, conjugation of antibodies to cytotoxins and endosome disruptive peptides can be performed. A vast range of monoclonal antibodies targeting CD44 and CD133 are commercially available for routine research applications. However, these antibodies can be prepared using hybridoma cell lines that are currently available. For small-scale studies of antibody conjugates in vitro, NHS esters of small molecules and peptides can be conjugated to Lys residues of IgG (150 KDa) using ca. 0.5 mg of IgG in 100 μL buffer. Spin columns, filled with sephadex G25 for gel filtration, can separate unreacted small molecules from the IgG. This sephadex retains molecules of less than 5 KDa. For larger endosome disruptive peptides and their linkers, sephadex G50, which binds proteins of less than 30 KDa, or other purification matrices (e.g. Protein G columns) can be used. Complete removal of unreacted NHS esters can be assessed by analytical HPLC. The concentration of the IgG conjugate can be quantified using a nanodrop UV instrument based on the absorbance and extinction coefficient at 280 nm and 405 nm for compounds containing the Pacific Blue fluorophore. This absorbance can be compared with the absorbance and extinction coefficient for IgG alone, or other small molecules alone (if they have a distinctive UV signature), to quantify the drug-antibody ratio (DAR). Conjugates can also be analyzed by cleavage of a portion followed by comparison with an authentic standard by HPLC to measure the DAR. Controlling this ratio is critical to maintain long circulating half-lives of antibodies in vivo. It has been established that when more than four to six drugs are added to each IgG molecule, poor pharmacokinetic (PK) profiles are observed. For this reason, the ADC Kadcyla (mean elimination $T_{1/2}$=4 days), which is conjugated on some of its 80 Lys residues using NHS chemistry, is prepared with a DAR of 3.5. This prevents substantial deviation from the favorable PK of the unmodified IgG (i.e. Herceptin mean elimination $T_{1/2}$=6 days).

Antibodies generated from hybridomas can be purified by chromatography on protein A/G columns. Purified antibodies can be conjugated to NHS-esters of disulfide-containing cytotoxins or endosome disruptive peptides. The resulting conjugates can be purified again with gel filtration or Protein A/G columns. Conjugates can be analyzed by UV spectroscopy to determine drug loading and aliquots treated with DTT or cathepsin B to release the cytotoxin or peptide and allow analysis by reverse phase HPLC ESI-MS. Additionally, in vitro assays can be performed that ensure that treatment with reduced glutathione at physiological concentrations (~5 mM) will efficiently release the cargo from the antibody under conditions that simulate cleavage of the disulfide in endosomes. Release can be monitored by reverse phase analytical HPLC, and the identity of the products can be confirmed by ESI-MS. NHS esters can be used for conjugation, and disulfides and protease substrates can be used as cleavable linkers.

Figure 7A:
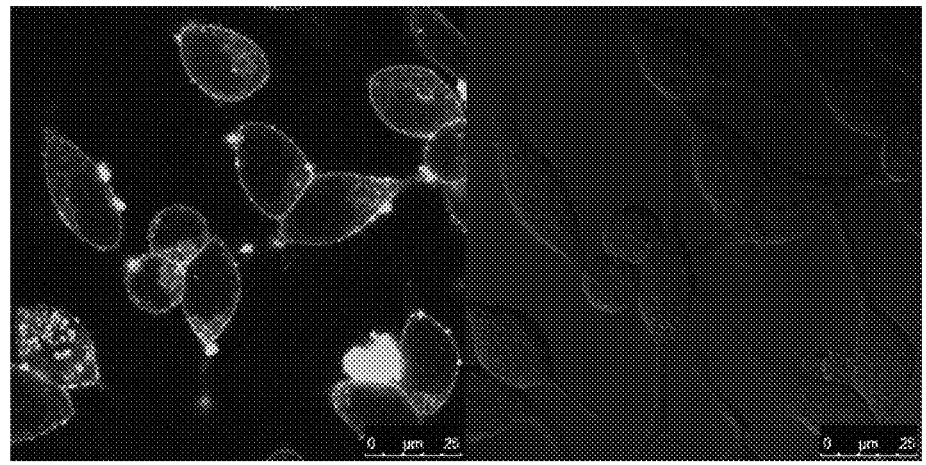
FIG. 7A shows confocal fluorescence and DIC micrographs of LnCaP cells treated with the targeted fluorophore F (5 µM) for 18 hr (i) and F (5 µM)+the targeted endosome disruptive peptide ED217 (5 µM) for 18 hr (ii).
Figure 7A:
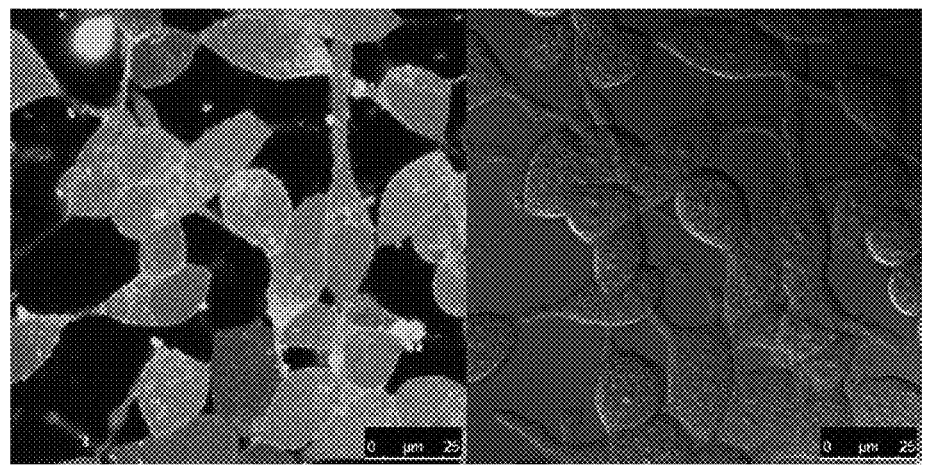
Figure 7B:
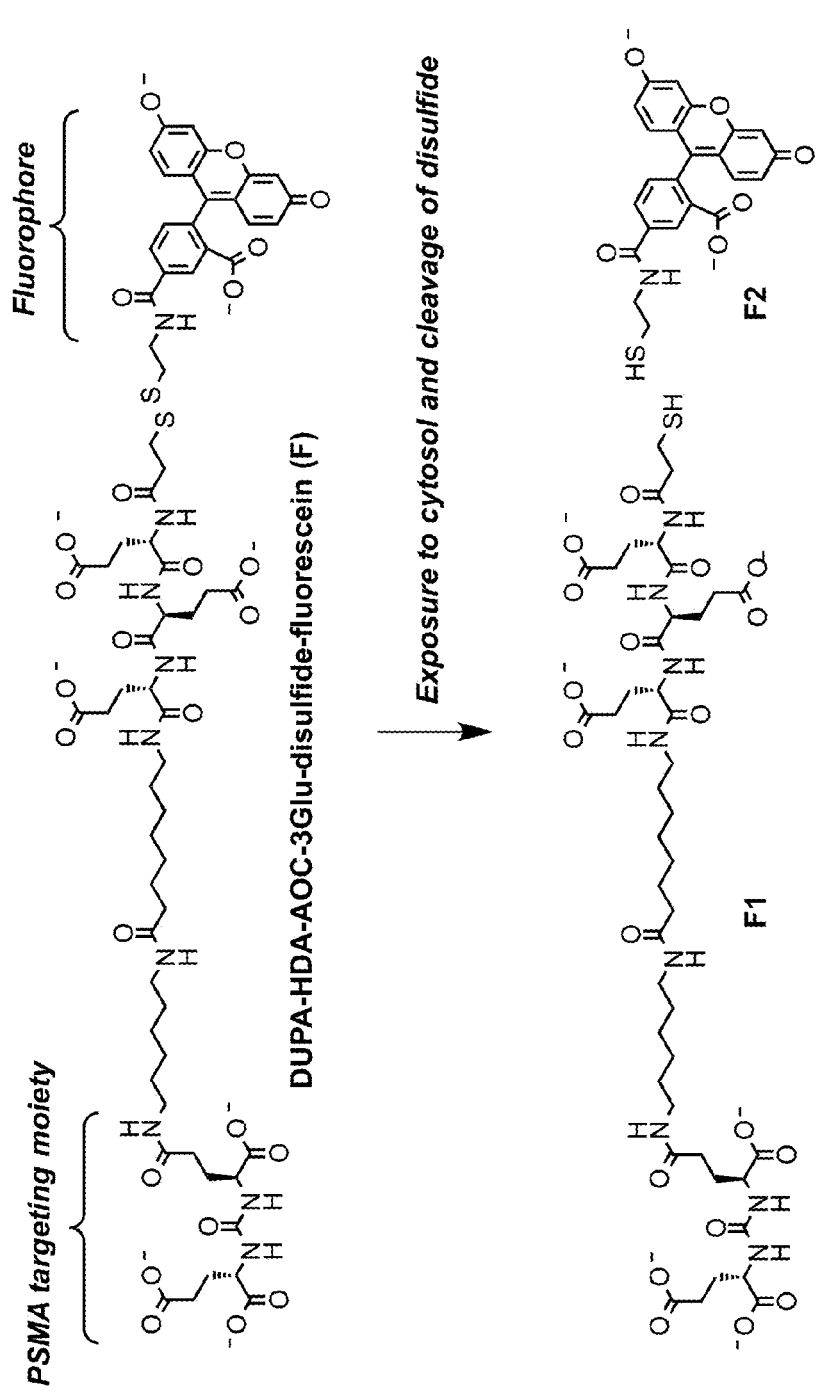
FIG. 7B shows the structure of the DUPA-HDA-AOC-3Glu-Disulfide Fluorescein (F), and the products of cleavage (F1, F2) by reduced glutathione (GSH).
Figure 7C:
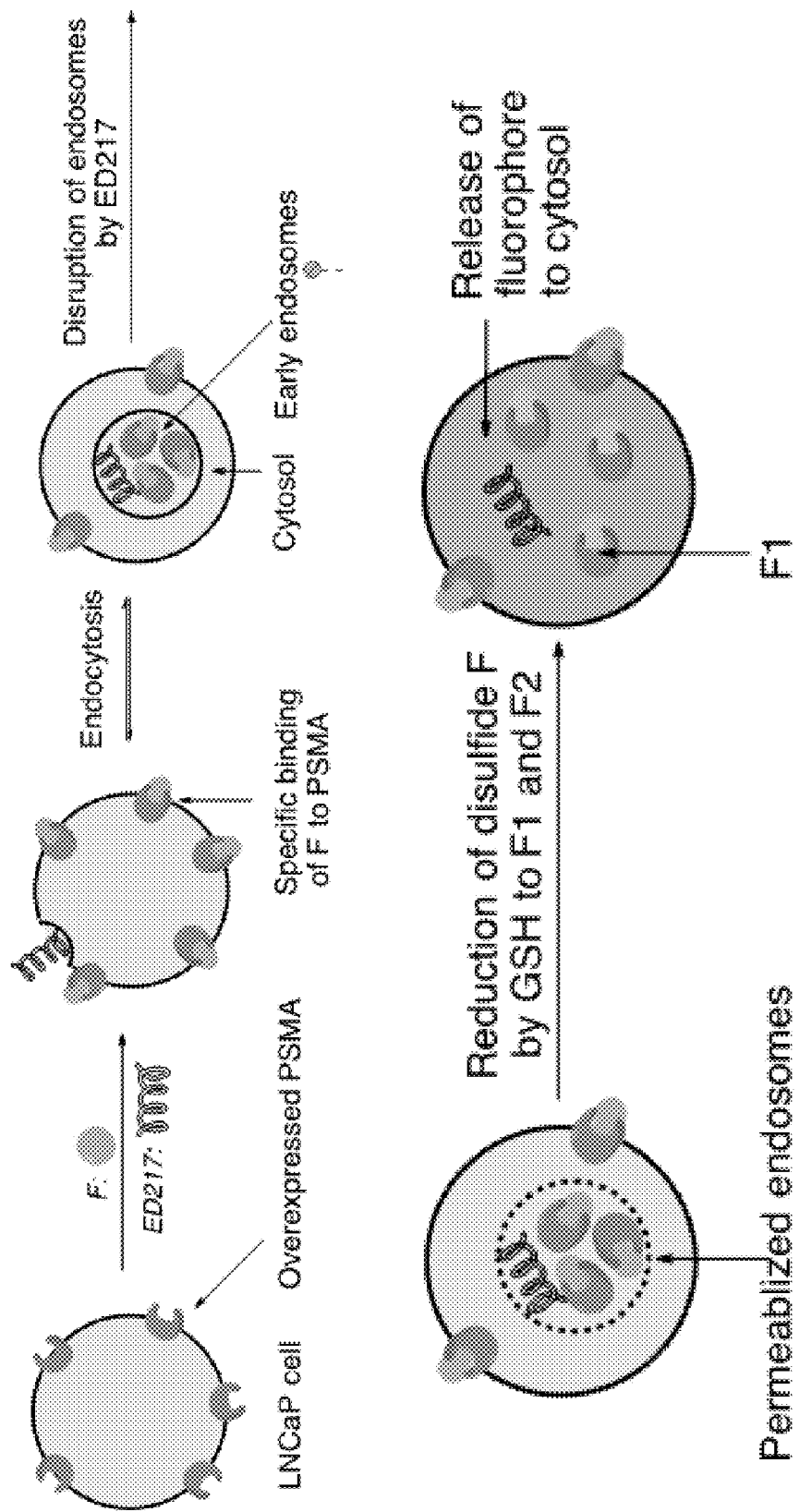
FIG. 7C shows a proposed mechanism of release of fluorophore F2 upon disruption of early endosomes.

In FIGS. 7A-7C, it can be seen that the use of a first delivery platform having a small molecule targeting moiety (e.g., DUPA) can be used for co-targeting with a second delivery platform having a cholesterol-linked endosome disruptive peptide (e.g., ED217) for a dual targeting application. Here, the DUPA targeting moiety (e.g., F) is linked through a linker to a reporter (e.g., fluorophore), however, it can be linked to any cargo, such as a drug moiety or toxic moiety. The DUPA targeting moiety is administered with a second delivery platform having a cholesterol-linked endosome disruptive peptide (e.g., ED217). FIG. 7A shows confocal fluorescence and DIC micrographs of LnCaP cells treated with F (5 μM) for 18 hr (i) and F (5 μM)+ED217 (5 μM) for 18 hr (ii). FIG. 7B shows the structure of the DUPA-HDA-AOC-3Glu-Disulfide Fluorescein (F), and the products of cleavage (F1, F2) by reduced glutathione (GSH). FIG. 7C shows a proposed mechanism of release of fluorophore F2 upon disruption of early endosomes. This shows that small molecules can be used as receptor targeting moieties. Thus, the present invention can extend to dual platform delivery systems, where each platform has a different targeting moiety, such as receptor targeting moieties and/or membrane targeting moieties.

Figure 8:
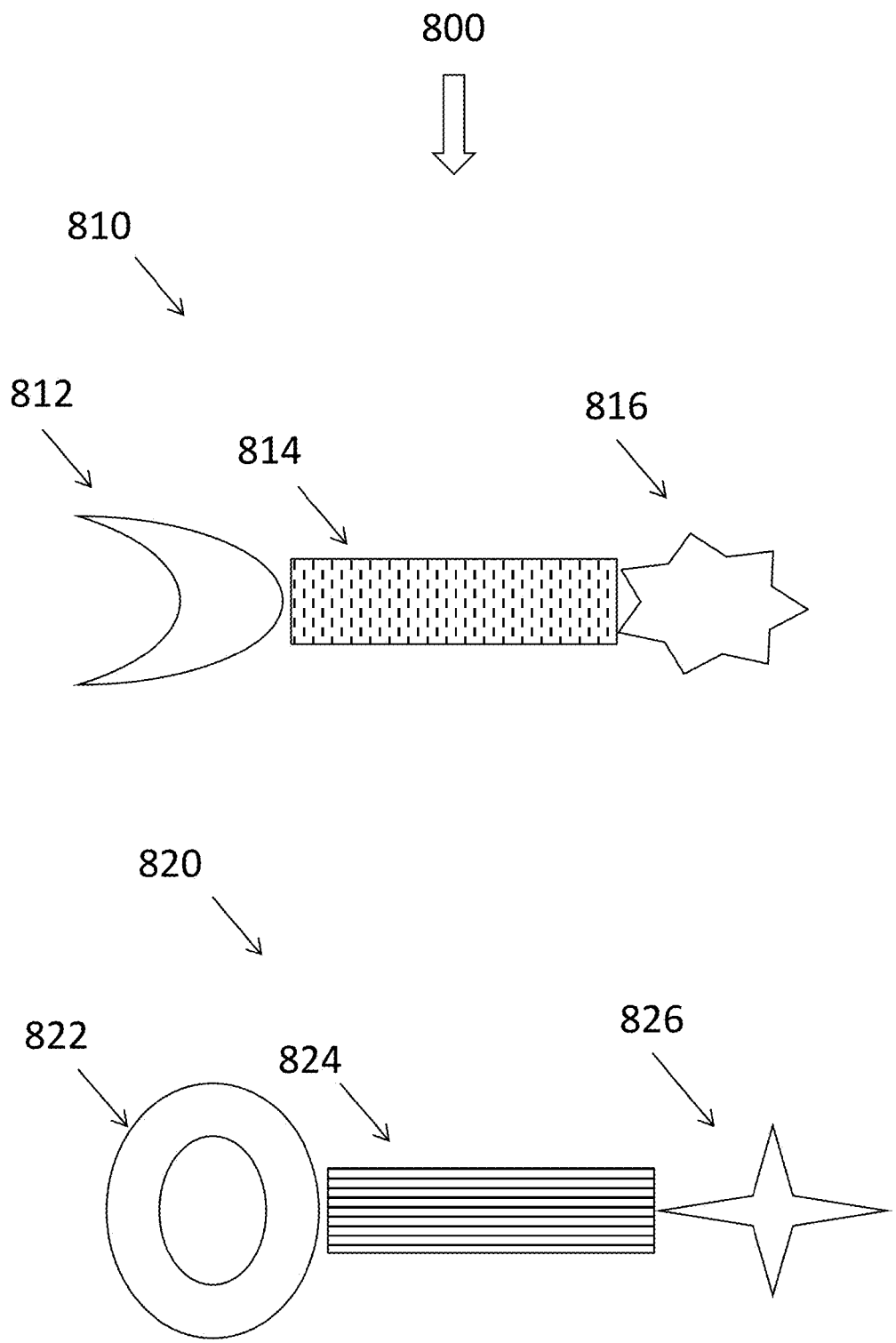
FIG. 8 illustrates an example of a dual platform delivery system that has two different platforms, each platform having a different targeting moiety, with one platform having a degradable linker and cargo agent for delivery into cytosol and one platform having an endosome disruptor.

FIG. 8 illustrates a dual platform delivery system 800 having two different delivery platforms 810 and 820. The first delivery platform 810 includes a first targeting moiety 812 linked through a linker 814 to a cargo 816. The second delivery platform 820 includes a second targeting moiety 822, linked through a linker 824, to an endosome disruptor 826. Either one or both of the linkers 814, 824 can be cleavable, such as being selectively cleavable. However, the linker 814, linked to the cargo 816, may always be cleavable so that the cargo 816 can escape into the cytoplasm, when triggered by disruption of endosomes. Also, the linker 824 lined to the endosome disruptor 826 may not be cleavable, but be a stable linker that does not readily degrade in an endosome or lysosome. The first targeting moiety 812 is different from the second targeting moiety 822. However, both the first targeting moiety 812 and second targeting moiety 822, may be the same type (e.g., both antibodies) or different types (e.g., one an antibody and one a small molecule); both may target receptors; both may target membranes; or one can target a receptor and the other target a membrane. Thus, various configurations can be used for the dual platform delivery system 800.

In one embodiment, a delivery system for targeting two different receptors on a cell can be configured so as to cause endocytosis of the delivery system, destabilizing an endosome of the cell having the delivery system, and delivering a cargo agent from the destabilized endosome into cytosol of the cell. The delivery system can include: a first delivery platform and a separate second delivery platform, the first delivery platform having a first receptor targeting moiety linked to an endosome disrupting moiety through a first linker; and a second delivery platform having a different second receptor targeting moiety linked to a cargo agent through a second linker.

In one embodiment, a dual platform delivery system can include: a first delivery platform comprising a first receptor targeting moiety linked to an endosome disrupting moiety through a first linker; and a separate second delivery platform comprising a different second receptor targeting moiety linked to a cargo agent through a second linker.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: at least one of the first or second membrane binding element is a receptor targeting moiety; and the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome; and the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein one of the first and second membrane binding elements targets a specific receptor on the cell and the other is a general targeting moiety; and the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein one of the first and second membrane binding elements targets a specific receptor on the cell and the other targets a non-specific receptor on the cell; and the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein one of the first and second membrane binding elements targets a specific receptor on the cell and the other targets a different specific receptor or non-specific receptor on the cell, wherein the combination of the specific receptor and different specific receptor or non-specific receptor on the cell are selective for targeting certain types of cells; and the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein the first membrane binding element targets a first specific receptor on the cell and the second membrane binding element targets a different second specific receptor on the cell, wherein the combination of the first specific receptor and different second specific receptor are selective for targeting certain types of cells; and the first and second linker may be the same or different.

In one embodiment, the delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein the first membrane binding element is an antibody targeting moiety that targets a first specific receptor on the cell and the second membrane binding element targets a different second specific receptor on the cell, wherein the combination of the first specific receptor and different second specific receptor are selective for targeting certain types of cells; and the first and second linker may be the same or different.

In one embodiment, a delivery system for introducing a cargo agent into cytosol of a living cell: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein the first membrane binding element is a first antibody targeting moiety that targets a first specific receptor on the cell and the second membrane binding element is a different second antibody targeting moiety targets a different second specific receptor on the cell, wherein the combination of the first specific receptor and different second specific receptor are selective for targeting certain types of cells; and the first and second linker may be the same or different.

In one embodiment, a delivery system for introducing a cargo agent into cytosol of a living cell can include: a first delivery platform having a first membrane binding element linked to an endosome disrupting moiety through a first linker; and a second delivery platform having a different second membrane binding element linked to a cargo agent through a second linker, wherein: the first and second membrane binding elements associate with different features on the same cell so as to induce endocytosis of the first and second delivery platforms into the same endosome, wherein the first membrane binding element is an antibody targeting moiety that targets a first specific receptor on the cell and the second membrane binding element is a cholesterol targeting moiety that targets a different second specific receptor on the cell, wherein the combination of the first specific receptor and different second specific receptor are selective for targeting certain types of cells; and the first and second linker may be the same or different.

In one aspect, the first membrane binding element is a first receptor targeting moiety and the second membrane binding element is a different second receptor targeting moiety. In one aspect, the first membrane binding element is a first targeting moiety and the second membrane binding element is a different second targeting moiety.

In one embodiment, the first and/or second linker has one or more anionic moieties. In one aspect, the first and/or second linker has one or more glutamic acid moieties. In one aspect, the first and/or second linker has one or more beta alanine moieties. In one aspect, the first and/or second linker has one or more anionic moieties and one or more beta alanine moieties between the one or more one or more anionic moieties and the first or second targeting moieties. In one aspect, the first and/or second linker has one or more anionic moieties and one or more beta alanine moieties between the one or more one or more glutamic acid moieties and the first or second targeting moieties. In one aspect, the first and/or second linker has one or more anionic moieties and one or more beta alanine moieties between the one or more one or more anionic moieties and the first or second targeting moieties. In one aspect, the first and/or second linker has one or more anionic moieties and one or more beta alanine moieties between the one or more one or more glutamic acid moieties and the first or second targeting moieties, at least one of the first or second targeting moieties is a cholesterol-type targeting moiety.

In one embodiment, the second linker has a region that is selectively cleavable. This allows the cargo to detach and enter the cytocol once the endosome is destabilized. In one aspect, the linker has a region that is selectively cleavable by a protease. In one aspect, a linker has a region that is selectively cleavable by a protease of a particular type of cell. In one aspect, a linker has a region that is cleavable by acidification. In one aspect, a linker has a region that is a selectively cleavable disulfide.

In one embodiment, the first and second targeting moieties both induce endocytosis into the same endosome.

In one embodiment, the endosome disrupting moiety destabilizes the endosome having the cargo agent such that the cargo agent is released into the cytosol of the cell. In one aspect, the endosome disrupting moiety is a polypeptide. In one aspect, the endosome disrupting moiety includes a polypeptide that comprises a PC4 peptide, PC4 peptide related sequence, PC4 D-peptide variant, a peptidomimetic, or derivative thereof. In one aspect, the endosome disrupting moiety includes the PC4 peptide with an amino sequence SSAWWSYWPPVA (SEQ ID NO: 1), or derivative or mutant thereof. In one aspect, the endosome disrupting moiety includes a conformationally constrained polypeptide. In one aspect, the endosome disrupting moiety includes a conformationally constrained kinked polypeptide.

In one embodiment, one of the first and second targeting moieties is a cholesterylamine or derivative thereof; or dihydrocholesterylamine or derivative thereof; or cholesterol carbamate or derivative thereof.

In one embodiment, one of the first and second targeting moieties is a N-alkyl-cholesterylamine derivative or 3β-amino-5alpha-cholestane or derivative thereof.

In one embodiment, the cargo agent is selected from the group consisting of cytotoxins, drugs, prodrugs, molecular probes, polypeptides, proteins, polynucleotides, DNA, RNA, siRNA, PNA, morpholinos, carbohydrates, or lipids, and combinations thereof. In one aspect, the cargo agent is a chemotherapeutic agent and at least one of the targeting moieties selectively targets cancer cells.

In one embodiment, the cargo agent is a chemotherapeutic agent and both of the targeting moieties selectively targets particular cancer cells. In one aspect, one of the first or second targeting moiety targets EGFR and the other targets HER2.

In one embodiment, one of the first or second targeting moiety is derived from EGF or an antibody against EGFR and the other is derived from the Herceptin antibody against HER2.

In one embodiment, at least one of the first or second targeting moiety is selected from targeting moieties that target EGFR, HER2, CD30, CD44, CD133, PSMA, PDGFR, TFR, LDLR, and FOLR.

In one embodiment, the first and second delivery platforms are separate entities. That is, they are not linked together via covalent bonds.

In one embodiment, the first and second delivery platforms target different cell surface receptors that cycle through common endosomes.

In one embodiment, the first delivery platform is devoid of a cargo agent; and/or the second delivery platform is devoid of an endosome disrupting moiety.

In one embodiment, the first or second targeting moiety is an antibody, antibody fragment, aptamer, nucleic acid, folate, or the like. In one aspect, the first or second targeting moiety is a receptor specific targeting moiety and the other is a generic cell targeting moiety.

In one embodiment, the first delivery platform and second delivery platform are not a bispecific antibody.

In one embodiment, the first or second targeting moiety is Trastuzumab (i.e., Herceptin).

In one embodiment, the first or second targeting moiety is Brentuximab.

In one embodiment, the first or second targeting moiety targets prostate-specific membrane antigen.

In one embodiment, the first or second targeting moiety targets EGFR.

In one embodiment, at least one of the first or second targeting moiety is an aptamer.

In one embodiment, the first and second targeting moieties inhibit off-targeting of off-target cells.

In one embodiment, the first or second targeting moieties are synergistically selective for a particular cell type.

In one aspect, at least one of the first or second targeting moiety is an aptamer having a sequence that allows for targeting and associating a particular cell surface receptor.

In one embodiment, a method of delivering a cargo agent into cytosol of a cell can include: providing the delivery system of one of the embodiments provided herein having the first and second delivery platforms; and administering the delivery system to a cell so as to cause targeting of two different receptors on the cell so as to cause endocytosis of the delivery system into an endosome, destabilizing the endosome of the cell having the delivery system, and delivering the cargo agent from the destabilized endosome into cytosol of the cell. In one aspect, the first and second delivery platforms are specific for targeting a specific cell type. In one aspect, the method of delivering cargo to cytosol of a cell can be used in a method of treating a disease. Such a therapeutic method can include: performing the method of delivering cargo to cytosol of a cell in a subject having a disease, wherein the cargo agent is a therapeutic agent for the disease.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

U.S. Pat. No. 8,637,468.

U.S. 2010/0041773.

WO 2014/055754.

This cross-references Provisional U.S. Application 61/710,289, which application is incorporated herein by specific reference in its entirety.

The invention claimed is:

1. A dual platform delivery system for targeting a cell, the delivery system comprising:
   a first delivery platform having a first targeting moiety linked to an endosome disrupting moiety through a first linker; and
   - a second delivery platform having a second targeting moiety linked to a cargo agent through a second linker, wherein the first targeting moiety is a different targeting moiety from the second targeting moiety, the second delivery platform being separate from the first delivery platform,
   - wherein the delivery system is configured so as to cause endocytosis of the first delivery platform and second delivery platform in a common endosome, destabilize the endosome, and release the cargo agent from the destabilized endosome into cytosol of the cell, wherein at least one of the first targeting moiety or second targeting moiety is a receptor targeting moiety that targets a receptor on the cell
   - wherein at least one of the first targeting moiety or second targeting moiety is a nucleic acid aptamer targeting moiety.

2. The delivery system of claim 1, wherein:
   - the first delivery platform includes the first targeting moiety as a first receptor targeting moiety; and
   - the second delivery platform includes the second targeting moiety as a different second receptor targeting moiety.

3. The delivery system of claim 1, wherein:
   - the first delivery platform includes the first targeting moiety as a first membrane binding element; or
   - the second delivery platform includes the second targeting moiety as a second membrane binding element.

4. The delivery system of claim 1, wherein:
   - the first targeting moiety and second targeting moiety each associate with different features on the same cell so as to induce endocytosis of the first and second delivery platforms into the same endosome.

5. The delivery system of claim 1, wherein:
   - the first targeting moiety and second targeting moiety each associate with different features on the same cell so as to induce endocytosis of the first and second delivery platforms into the same endosome, wherein one of the first targeting moiety or second targeting moiety targets a specific receptor on the cell.

6. The delivery system of claim 1, wherein:
   - the first targeting moiety and second targeting moiety each associate with different features on the same cell so as to induce endocytosis of the first and second delivery platforms into the same endosome, wherein one of the first targeting moiety or second targeting moiety targets a specific receptor on the cell and the other targets a non-specific feature on the cell.

7. The delivery system of claim 1, wherein:
   - the first targeting moiety and second targeting moiety each associate with different features on the same cell so as to induce endocytosis of the first and second delivery platforms into the same endosome, wherein the first targeting moiety targets a first specific receptor on the cell and the second targeting moiety targets a different second specific receptor on the cell, wherein the combination of the first specific receptor and different second specific receptor are selective for targeting a specific type of cell.

8. The delivery system of claim 1, wherein one of the first targeting moiety or second targeting moiety is a small molecule targeting moiety.

9. The delivery system of claim 1, wherein the first targeting moiety and second targeting moiety are different nucleic acid aptamer targeting moieties.

10. The delivery system of claim 1, wherein one of the first targeting moiety or second targeting moiety is a membrane binding moiety.

11. The delivery system of claim 1, wherein the second linker has a region that is selectively cleavable.

12. The delivery system of claim 1, wherein the first linker has a region that is stable in an endosome.

13. The delivery system of claim 1, wherein the endosome disrupting moiety is a polypeptide.

14. The delivery system of claim 1, wherein the cargo agent is selected from the group consisting of cytotoxins, drugs, prodrugs, molecular probes, polypeptides, proteins, polynucleotides, DNA, RNA, siRNA, PNA, morpholinos, carbohydrates, or lipids, and combinations thereof.

15. A method of delivering a cargo agent into cytosol of a cell, the method comprising:
   - providing the delivery system of claim 1 having the first and second delivery platforms; and
   - administering the delivery system to a cell so as to cause targeting of two features on the cell so as to:
   - cause endocytosis of the first and second delivery platforms of the delivery system into a common endosome,
   - destabilize the endosome of the cell having the delivery system,
   - release the cargo agent from the second linker; and release the cargo agent from the destabilized endosome into cytosol of the cell.

16. The method of claim 15, wherein the first and second delivery platforms are specific for targeting a specific cell type.

17. A method of treating a disease in a subject, comprising:
   providing the delivery system of claim 1 having the first and second delivery platforms; and
   administering the delivery system to the subject having the disease, wherein the cargo agent is a therapeutic agent for the disease,
   wherein said disease is treated.

\* \* \* \* \*